United States Patent
McDougall

(10) Patent No.: US 6,983,507 B2
(45) Date of Patent: Jan. 10, 2006

(54) TOOTHBRUSH

(75) Inventor: Gregory McDougall, Angeles (PH)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/373,738

(22) Filed: Feb. 27, 2003

(65) Prior Publication Data

US 2004/0168271 A1    Sep. 2, 2004

(51) Int. Cl.
  A61C 17/16    (2006.01)
  A46B 13/00    (2006.01)
  A47L 13/12    (2006.01)

(52) U.S. Cl. .............. 15/22.1; 15/22.2; 15/28; 15/110; 15/180

(58) Field of Classification Search ........... 15/21.1, 15/22.2, 28, 167.1, 179, 180, 176.1, 110; 601/139, 141–142; D4/109–110, 104, 127
See application file for complete search history.

(56) References Cited

U.S. PATENT DOCUMENTS

| 3,195,537 A | * | 7/1965 | Blasi ...................... 601/114 |
| 4,571,768 A | | 2/1986 | Kawashima |
| 5,625,916 A | * | 5/1997 | McDougall .................. 15/28 |
| 5,628,082 A | | 5/1997 | Moskovich |
| 5,652,990 A | | 8/1997 | Driesen et al. |
| 6,021,538 A | * | 2/2000 | Kressner et al. ............ 15/28 |
| 6,446,295 B1 | * | 9/2002 | Calabrese .................. 15/28 |
| D487,636 S | * | 3/2004 | De Salvo ................ D4/101 |
| 6,820,299 B2 | | 11/2004 | Gavney, Jr. |
| 6,820,300 B2 | | 11/2004 | Gavney, Jr. |
| 2003/0033680 A1 | * | 2/2003 | Davies et al. ............ 15/22.1 |

FOREIGN PATENT DOCUMENTS

| GB | 2 371 217 A | * | 7/2002 |
| WO | 03/0434359 | | 5/2003 |

* cited by examiner

Primary Examiner—John Kim
Assistant Examiner—Laura C Cole
(74) Attorney, Agent, or Firm—Harris A. Wolin

(57) ABSTRACT

An electrically-driven toothbrush has a brush holder that is arranged to rotationally vibrate and carry a number of bristles interspaced with arcuate membranes. The membranes serve to aid cleaning of the teeth and to polish the teeth surfaces during use of the toothbrush.

31 Claims, 3 Drawing Sheets

TOOTHBRUSH

BACKGROUND OF THE INVENTION

The invention relates to toothbrushes.

The invention relates more particularly to electrically-driven toothbrushes in which brush bristles are arranged to move relative to an elongated toothbrush handle such that the bristles rotate about an axis generally at right angles to a longitudinal axis of the handle. The bristles may rotate completely or preferably oscillate as fully described, for example, in U.S. Pat. No. 5,625,916.

In certain conditions, the overall cleaning effect of such brushes is not wholly satisfactory, especially for polishing the teeth or removing stains.

It is an object of the invention to overcome or to at least reduce this problem.

SUMMARY OF THE INVENTION

According to one aspect of the invention, there is provided an electrically-driven toothbrush having an elongated handle and a brush head mounted to a remote end of the handle, a bristle holder rotatably mounted to the brush head to rotate about an axis generally at right angles to the longitudinal axis of the handle, including an array of upstanding bristles interspaced with a number of separate upstanding flexible membranes that are arranged such as to rub against surfaces of teeth during brushing.

The membranes are preferably shorter than at least the longest of the bristles.

Each membrane is preferably arcuate in cross-section and partially surrounds a respective bristle of the bristle array.

Each membrane may be semicircular in cross-section and positioned between a respective bristle and the rotational axis of the brush holder.

The membranes are preferably evenly distributed about the brush holder axis and each partially surrounds a respective peripherally-sited bristle of the bristle array.

There are typically five membranes and at least ten bristles.

The membranes may be formed of plastic material.

According to another aspect of the invention there is provided a rotatable bristle holder for an electrically-driven toothbrush having an array of upstanding bristles interspaced with a number of separate upstanding flexible membranes arranged such as to rub against surfaces of the teeth during brushing.

An electric toothbrush according to the invention will now be described by way of example with reference to the accompanying drawings.

DETAILED DESCRIPTION

Figure 1:
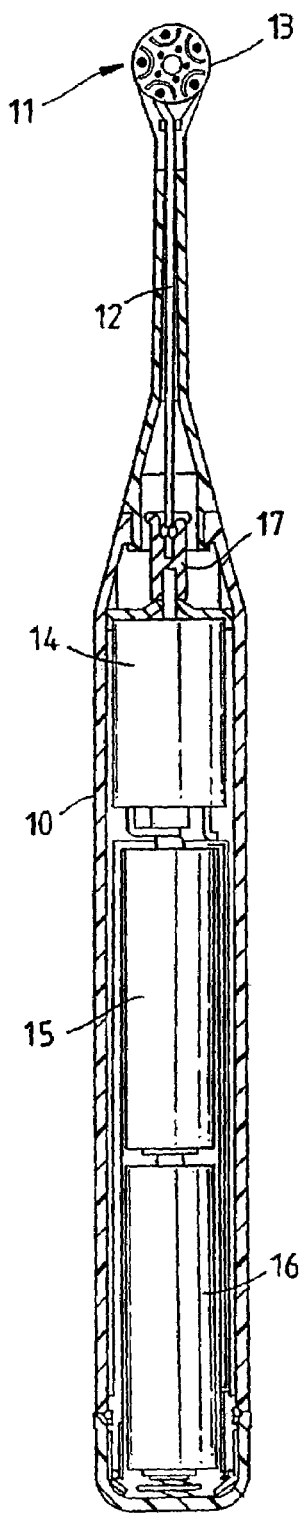
FIG. 1 is a sectional bottom view of the toothbrush.

Referring to the drawings, in FIG. 1 the toothbrush comprises a handle portion 10 at a first end of the toothbrush, a brush head 11 at a second end of the toothbrush, a rotatable shaft 12 extending from the handle to the head, and a generally circular bristle holder 13. The handle provides compartments for holding an electric motor 14 and two batteries 15 and 16. A shaft coupling 17 is arranged to grip one end of the shaft 12 and allow the shaft to be pulled out for cleaning or replacement.

Figure 2:
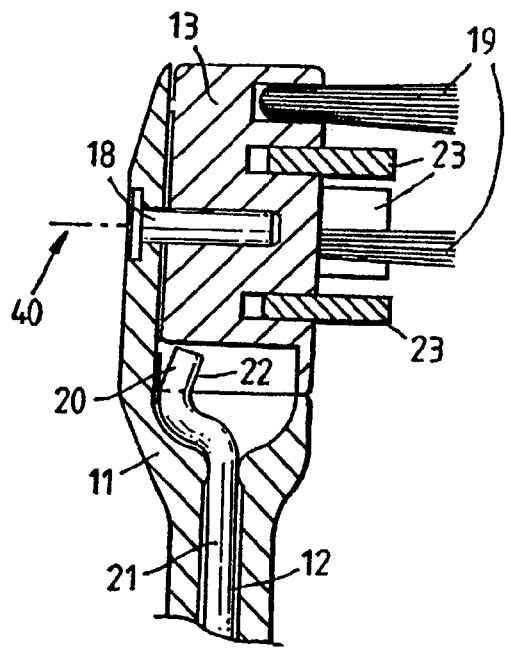
FIG. 2 is a cross-sectional side view of a brush head of the toothbrush.

The head 11, as is better seen in FIG. 2, supports a post 18 which provides a rotational pivot axis 40 for the bristle holder 13. Bristles 19 are shown for illustrative purpose only in FIG. 2. The shaft 12 has an integrally formed remote-most end 20 that is off-set from a central longitudinal axis 21 of the shaft.

Figure 3:
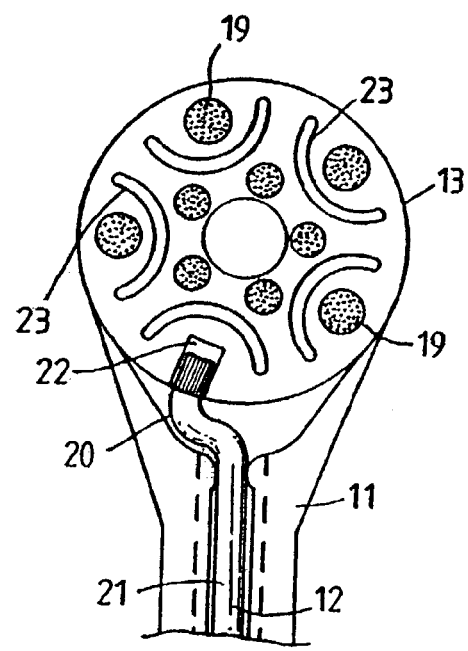
FIG. 3 is a plan view of FIG. 2.

The remote-most end 20 fits a slot 22 (see FIG. 3) formed in a side of the bristle holder 13. It will be noted that the end 20 points towards an intersection of the first axis 21 and a second central axis 40 of the post 18. When the shaft 12 is rotated by the motor 14, the remote end 20 describes a circle about the shaft 12 and drivingly engages the slot 22 to cause the bristle holder 13 to rotationally vibrate. As may be seen in FIG. 3, the slot 22 is closed-ended and extends radially inward from the outer circumference of the holder to less than the distance to the center of the holder. Thus, the holder 13 pivots or rotates forwards and backwards about the center of the post 18. Such vibrations comprise the relative motion between the head 11 and the bristles 19 and is generally beneficial for efficient cleaning of teeth. The width of the slot 22 is preferably generally the same as the diameter of the end 20 to leave minimum play; this keeps noise to a minimum while in use.

FIG. 1 shows a toothbrush where the holder 13 vibrates or rotates through an angle of 30°. In FIG. 2 the angle is 35°. It will therefore be appreciated that the rotational angle can be chosen by fitting different shafts 12 and that the same bristle holder can be used for all angles. It is also possible to use the holder 13 in a toothbrush where the holder is oscillated through 60° or 120° or rotated through 360° in continuous rotation.

The described shaft 12 is preferably integrally formed, i.e., a single length of a thin rod and shaped as shown. However, it is possible to arrange for the remote end 20 to be separately formed or provided and fixed to a straight end part of the shaft. Such a separate part can be a brush having a central axis coinciding with the axis 21 of the shaft and an off-center driving post.

The driving post then takes up the position and function of the remote end 20. Thus, the driving post and the slot 22 then form the driving engagement between the shaft and the holder 13 and so the driving post can be regarded as the remote end of the shaft.

Figure 4:
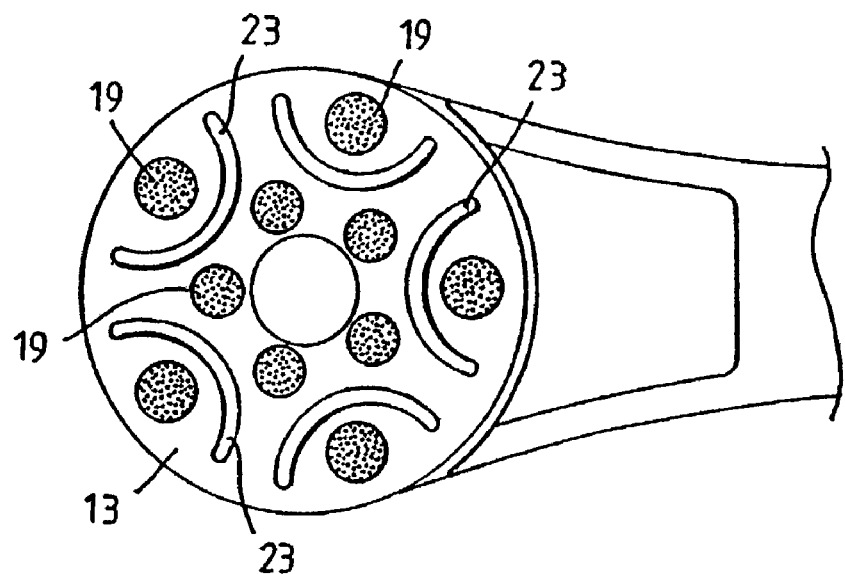
FIG. 4 is an enlarged top plan view of the brush head.
Figure 5:
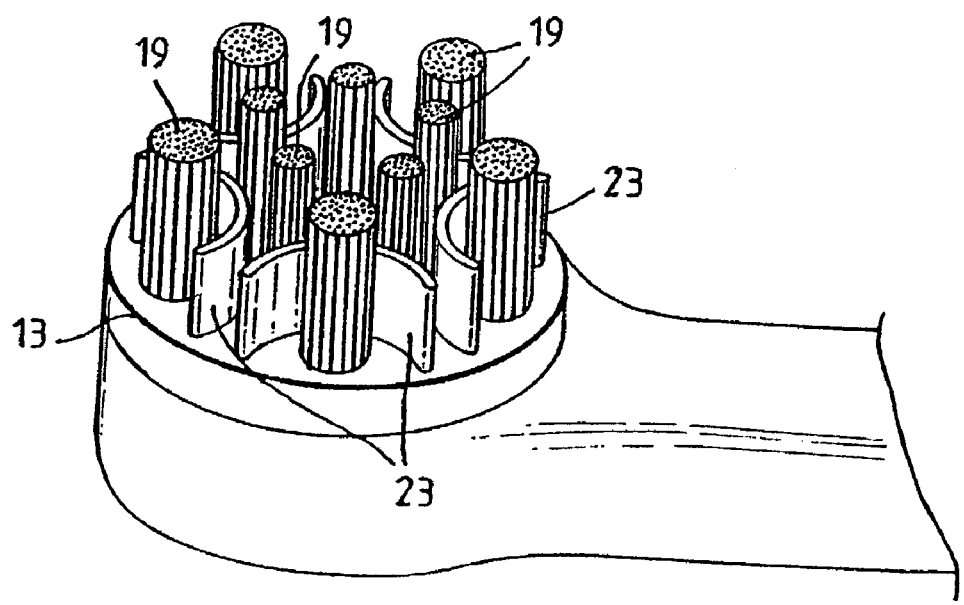
FIG. 5 is an isometric view of FIG. 4.

In FIGS. 4 and 5, an electrically driven toothbrush has a brush holder 13 that is arranged to rotationally vibrate and carry a number of bristles 19 interspaced with arcuate membranes 23. The membranes serve to aid cleaning of the teeth and to polish the teeth surfaces during use of the toothbrush.

As shown in FIGS. 4 and 5, the brush holder 13 carries ten bristles that are interspaced by five flexible membranes 23. Each membrane is generally semicircular in cross-section and partially surrounds a respective bristle mounted adjacent the periphery of the brush holder. The membranes 23 are positioned between the respective bristles and the central axis 40 of the brush holder. In such a configuration, the membranes are inherently unlikely to become clogged up with toothpaste or debris removed from the teeth.

The peripheral bristles are preferably thicker than the inner bristles, which may be shorter in length than the peripheral bristles. The membranes 23 are generally shorter than all the bristles and typically protrude up about 50% to 90% of the height of the bristles they partially surround. The membranes are formed of food-safe plastic material, such as neoprene or other synthetic rubber, but may be made of woven fabric or similar.

The membranes rub against the surfaces of the teeth and serve to polish surfaces of the teeth and remove stains during use. The membranes may be reasonably effective in this respect if they are generally rectangular in cross-section, or completely surround some or all of the bristles, or more completely surround than shown in the figures.

What is claimed is:

1. A toothbrush comprising a power source, a handle and a head defining a periphery connected to the handle, the head including a plurality of tooth cleaning elements, a central axis and further comprising a holder rotatably mounted to the head for rotation of the holder about the central axis, and, the plurality of tooth cleaning elements including a bristle element and a plurality of flexible membranes provided on the holder, wherein each of said membranes on the holder has an arcuate section extending between opposing ends and each of the opposing ends is adjacent to the periphery of the head and disposed closer to the periphery than the center axis, in which the arcuate section has a concave side facing a periphery portion that the ends are adjacent to.

2. The toothbrush according to claim 1, in which at least one membrane has a first height defined from the holder, and said bristle element has a second height defined from the holder; wherein the first height ranges from about 50% to 90% of the second height.

3. The toothbrush according to claim 1, in which the bristle element is disposed adjacent to the periphery and between the opposing ends of at least one of the membranes.

4. The toothbrush according to claim 1, in which the bristle element is partially surrounded by at least one of the membranes.

5. The toothbrush according to claim 1, in which the arcuate section has a convex side opposing the concave side.

6. The toothbrush according to claim 1, in which the bristle element includes a first bristle tuft being disposed adjacent to the periphery and a second bristle tuft being disposed interior of the flexible membranes, the first bristle tuft extending farther from the base than the second bristle tuft.

7. The toothbrush according to claim 6, in which at least one of the membranes is shorter than the first bristle tuft and the second bristle tuft.

8. The toothbrush according to claim 1, in which the bristle element includes a first bristle tuft disposed adjacent to the periphery and a second bristle tuft being disposed interior of the flexible membranes, the first bristle tuft having a first thickness and the second bristle tuft having a second thickness, the first thickness being larger than the second thickness.

9. The toothbrush according to claim 8, in which the first bristle tuft extends farther from the holder than the second bristle tuft.

10. The toothbrush according to claim 8, in which at least one of the membranes is shorter than the first bristle tuft and the second bristle tuft.

11. The toothbrush according to claim 8, in which the head is configured to vibrate.

12. The toothbrush according to claim 8, wherein the holder supports the membrane and the first bristle tuft and the second bristle tuft.

13. A toothbrush comprising a power source, a handle and a head defining a periphery connected to the handle, the head having a central axis and a plurality of tooth cleaning elements, the plurality of tooth cleaning elements including a plurality flexible membranes and cleaning members, each of said membranes having opposing ends and a concave portion extending between the opposing ends, each of the opposing ends are closer to the periphery than the central axis, each concave portion facing the periphery portion that the ends are adjacent to, the cleaning members being adjacent to the periphery and disposed between the membranes, the head comprises a holder rotatably mounted to the head for rotation of the holder about the central axis, and wherein the holder supports the membranes and the cleaning members.

14. The toothbrush according to claim 13, in which at least one membrane has a first height, and at least one of the cleaning members has a second height; wherein the first height ranges from about 50% to 90% of the second height.

15. The toothbrush according to claim 13, in which at least one of the cleaning members comprises a bristle element, and said bristle element is disposed between the opposing ends of at least one of the membranes.

16. The toothbrush according to claim 13, in which at least one of the cleaning members comprises a bristle element and said bristle element is partially surrounded by at least one of the membranes.

17. The toothbrush according to claim 13, in which the cleaning members includes a first bristle tuft being disposed adjacent to the periphery and a second bristle tuft disposed between the membranes, the first bristle tuft extending farther than the second bristle tuft.

18. The toothbrush according to claim 17, in which at least one of the membranes is shorter than the first bristle tuft and the second bristle tuft.

19. The toothbrush according to claim 13, in which the cleaning members includes a first bristle tuft disposed adjacent to the periphery and a second bristle tuft disposed between the membranes, the first bristle tuft having a first thickness and the second bristle tuft having a second thickness, the first thickness being different from the second thickness.

20. The toothbrush according to claim 19, in which the first bristle tuft extends farther from the base than the second bristle tuft.

21. The toothbrush according to claim 19, in which at least one of the membranes is shorter than the first bristle tuft and the second bristle tuft.

22. The toothbrush according to claim 19, in which the at least one membrane has a first height and said first bristle tuft has a second height wherein the first height ranges from about 50% to 90% of the second height.

23. The toothbrush according to claim 19, in which the first thickness is larger than the second thickness.

24. The toothbrush according to claim 23, in which the first bristle tuft is partially surrounded by at least one of the membranes.

25. A toothbrush comprising a handle having a longitudinal axis, a head defining a periphery connected to the handle and a center axis generally perpendicular to the longitudinal axis, a power source the head including a surface and a plurality of flexible membranes extending from the surface, each of said membranes having opposing ends, a concave section and an opposing convex section, said sections being disposed between the opposing ends, wherein the concave sections face the periphery and the convex sections face the center axis, each of the ends of the membranes are adjacent to the periphery such that they are closer to the periphery than the center axis, and at least one of said membranes has at least one said end adjacent to one said end of another of said membranes.

26. The toothbrush according to claim 25, in which the head comprises a holder rotatably mounted to the head, wherein the holder supports the membranes of the surface.

27. The toothbrush according to claim 25, further comprising a bristle tuft and the membranes comprises a plastic material.

28. The toothbrush according to claim 27, in which the membranes are radially arranged on the head with respect to the center axis.

29. The toothbrush according to claim 25, wherein each said end is adjacent to one said end of another flexible membrane.

30. The toothbrush according to claim 29, wherein the power source is electric.

31. The toothbrush according to claim 30, in which the head comprises a holder rotatably mounted to the head, wherein the holder supports the membranes of the surface.

* * * * *